US009579484B2

(12) United States Patent
Barnell

(10) Patent No.: US 9,579,484 B2
(45) Date of Patent: Feb. 28, 2017

(54) STERILE MOLDED DISPENSER

(71) Applicant: Medtronic Vascular, Inc., Santa Rosa, CA (US)

(72) Inventor: Jeffrey Barnell, Santa Rosa, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 370 days.

(21) Appl. No.: 14/491,511

(22) Filed: Sep. 19, 2014

(65) Prior Publication Data

US 2016/0082223 A1 Mar. 24, 2016

(51) Int. Cl.
B65D 83/10 (2006.01)
A61B 17/06 (2006.01)
A61M 25/00 (2006.01)
A61M 39/16 (2006.01)

(52) U.S. Cl.
CPC .......... *A61M 25/002* (2013.01); *A61M 39/16* (2013.01); *A61B 50/30* (2016.02)

(58) Field of Classification Search
CPC ...... A61M 25/002; A61M 39/16; A61B 50/30
USPC ......... 206/363, 364, 438, 571; 604/523, 533
See application file for complete search history.

(56) References Cited

U.S. PATENT DOCUMENTS

| | | | | |
|---|---|---|---|---|
| 4,332,322 A | * | 6/1982 | Jaeschke | A61M 25/002 206/363 |
| 4,607,746 A | * | 8/1986 | Stinnette | A61M 25/002 206/363 |
| 5,840,151 A | * | 11/1998 | Munsch | B29C 53/32 156/379.8 |
| 5,848,691 A | | 12/1998 | Morris et al. | |
| 6,053,313 A | * | 4/2000 | Farrell | A61M 25/002 206/364 |
| 7,234,597 B2 | | 6/2007 | Rowe et al. | |
| 2005/0061698 A1 | * | 3/2005 | Delaney | A61M 25/002 206/364 |
| 2006/0186010 A1 | * | 8/2006 | Warnack | A61M 25/002 206/438 |
| 2006/0260967 A1 | * | 11/2006 | Clarke | A61F 2/0095 206/438 |

(Continued)

FOREIGN PATENT DOCUMENTS

EP 2468346 6/2012
WO WO2004/022433 3/2004

OTHER PUBLICATIONS

PCT/US2015/050779, The International Search Report and the Written Opinion of the International Searching Authority, mailed Dec. 8, 2015.

*Primary Examiner* — Luan K Bui

(57) ABSTRACT

A package for a medical device having an elongated shaft and a proximal luer fitting, the package includes a one-piece body formed as a single structure. The one-piece body includes at least a spiral casing formed therein, the spiral casing defining a spiral lumen configured to receive the elongated shaft of the medical device. The package includes a luer retaining portion at one end of the spiral casing with barrier film sealed to the luer retaining portion to maintain the sterility of the medical device. The package further including a cap placed over the luer retaining portion and barrier film to protect the integrity of the barrier film and prevent perforation of the barrier film which would compromise the sterility of the medical device.

21 Claims, 14 Drawing Sheets

(56) References Cited

U.S. PATENT DOCUMENTS

| | | |
|---|---|---|
| 2008/0183181 A1 | 7/2008 | Treacy et al. |
| 2011/0085775 A1 | 4/2011 | Van Zuylen et al. |
| 2012/0172846 A1* | 7/2012 | Nakamoto .......... A61M 25/002 |
| | | 604/533 |
| 2012/0261290 A1 | 10/2012 | Limjaroen et al. |
| 2013/0197618 A1 | 8/2013 | Cage et al. |
| 2013/0206623 A1* | 8/2013 | Spaargaren .......... A61B 19/026 |
| | | 206/363 |
| 2013/0327664 A1 | 12/2013 | Tanghoj |
| 2014/0262882 A1* | 9/2014 | Barnell ............... A61M 25/002 |
| | | 206/364 |

* cited by examiner

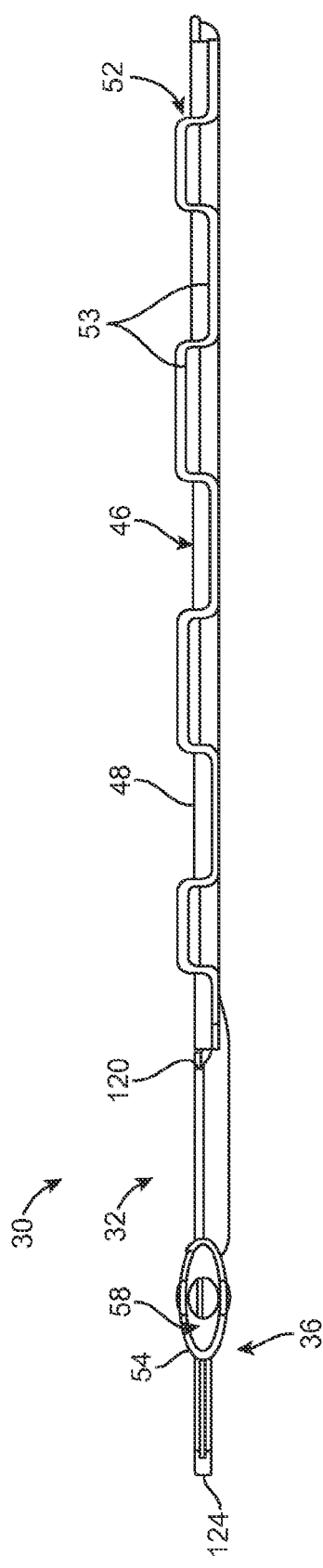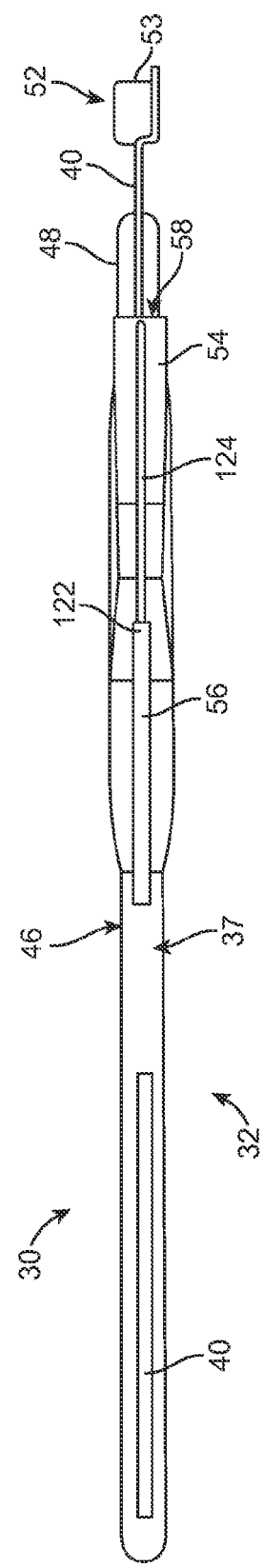

STERILE MOLDED DISPENSER

FIELD OF THE INVENTION

The present invention relates generally to catheters intended for deployment within a body lumen, such as a patient's vasculature, and more particularly, to packaging for a catheter.

BACKGROUND OF THE INVENTION

Catheters may be inserted into a patient's vasculature and deployed at various locations within the patient for a wide variety of purposes and medical procedures. For example, one type of catheter is used in percutaneous catheter intervention (PCI) for the treatment of a vascular constriction generally known as a stenosis. In this instance, the catheter has a distally mounted balloon that can be placed, in a deflated or unexpanded condition, within the stenosis, and then inflated or expanded to dilate the narrowed lumen of a blood vessel. This type of balloon dilation therapy is generally referred to as percutaneous transluminal angioplasty (PTA). When the treatment is more specifically intended for vessels of the heart, the process is known as percutaneous transluminal coronary angioplasty (PTCA). In other PCI procedures, a stent is expanded into contact with the vessel wall to prevent narrowing or restenosis of the artery.

For example, FIGS. 1 and 2 illustrate the deployment of a PTCA treatment catheter 16 within a patient's vasculature. To treat small diameter vessels remote from an entry point into a patient, a guiding catheter 10 may be used to span the distance. Guiding catheter 10 is typically inserted into a large artery 12 near the patient's groin and is then advanced towards the heart H to the entry opening or ostium of a diseased coronary artery. Guiding catheter 10 provides a conduit through which catheters and guidewires, such as treatment catheter 16 and a guidewire 18, can be passed from outside the patient to the vessel being treated. Treatment catheter 16 generally includes a flexible elongated tubular shaft and a luer fitting 14. For certain interventional procedures, treatment catheter 16 may include a dilatation balloon and/or a stent disposed along a distal portion thereof.

Referring now to FIGS. 3-4, catheters are commonly packaged and stored in a packaging hoop 11 as shown in FIG. 3 in accordance with the teachings of the prior art. Packaging hoop 11 consists of a coiled tube 13 having a proximal opening 17 through which treatment catheter 16 is inserted. Several clips 15 are coupled to tube 13 to maintain the tube in the coiled configuration. The overall diameter of packaging hoop 11 is selected to be as small as possible without imparting a lasting curve shape to the generally straight medical device during the shelf life thereof. An overly small diameter hoop 11 may also create excessive friction forces and thereby possibly cause product damage during loading or unloading of the medical device. Luer fitting 14, located at the proximal end of treatment catheter 16, has an area 19 that fits into proximal opening 17 of tube 13, as shown in FIG. 4, in order to secure treatment catheter 16 in packaging hoop 11 until it is removed for clinical use. One potential issue with utilizing clips 15 for holding tube 13 in the coiled configuration is that the packaging may not stay flat because clips 15 cannot grip tube 13 with much force without undesirably pinching or kinking the tubing and thereby restricting the loading and unloading of treatment catheter 16. Furthermore, tube 13 may separate from clips 15 during distribution.

In addition to coiled tube 13 and clips 15, catheter packaging typically requires additional parts or components such as a sealed pouch that completely envelopes the entire hoop 11. In addition, a sealed pouch further requires that the pouch be fully contained within a box or carton in order to protect the pouch. One potential issue with this packaging configuration is that the pouch can move inside the box during transport. This creates the possibility for the tube 13 or clips 15 to pierce the pouch and compromise the sterility of the catheter. If this were to occur, a breach of the pouch may be undetectable by the operator.

Accordingly, there remains a need in the art for improved packaging that overcomes these disadvantages of currently available catheter packaging, as well as a need to reduce the number of packaging components and the cost of packaging.

BRIEF SUMMARY OF THE INVENTION

Embodiments hereof relate to a package for holding and maintaining the sterility of a medical device that includes an elongated shaft. The package includes a blow-molded one-piece body or spiral casing that defines a spiral lumen configured to receive the elongated shaft of the medical device. A luer retaining portion is disposed at a first end of the spiral casing. More specifically, luer retaining portion is formed as a unitary continuation of the body such that the opening formed therein has no potential for a break in sterility where the interior of the luer retaining portion abuts or is connected with lumen. The luer retaining portion has a luer retainer defining an opening configured to receive the proximal luer fitting of the medical device. In one embodiment, a second end of the spiral casing has a closed distal end or tip thereof to seal the second end of the spiral casing.

In one aspect of the present invention, a barrier film is sealed to the luer retaining portion to maintain the sterility of the medical device disposed within the spiral casing. The barrier film is configured to be pulled or peeled apart to aseptically present the proximal luer fitting of the medical device to an operator. The barrier film is sealed by heat sealing, adhesives or ultrasonic welding to the luer retaining portion in a sterile environment to preserve the sterility of the medical device within the spiral casing.

In another aspect of the present invention, a cap with a rigid housing defining a chamber is placed over the luer retaining portion and barrier film to protect the barrier film from, for example, perforation during transport or storage. In one embodiment, the cap includes a locking member to releasably secure the cap to the luer retaining portion. The locking member has a clasp portion and a living hinge portion coupled together by a living hinge. The clasp portion rotates about the living hinge and has a pin receivable within an opening in the living hinge portion. The pin extends through the living hinge opening and through an opening in the luer retaining portion to secure the cap to the luer retaining portion. In a further embodiment, the clasp portion has an arcuate tongue which is receivable within a second opening in the luer retaining portion as the clasp portion is rotated about the living hinge. Once tongue is disposed within the second opening of the luer retaining portion, the tongue further prevents cap from being removed from the luer retaining portion.

BRIEF DESCRIPTION OF DRAWINGS

The foregoing and other features and advantages of the invention will be apparent from the following description of embodiments hereof as illustrated in the accompanying drawings. The accompanying drawings, which are incorporated herein and form a part of the specification, further serve to explain the principles of the invention and to enable a person skilled in the pertinent art to make and use the invention. The drawings are not to scale.

FIG. 6 is a side view of the package of FIG. 5.

FIG. 6A is a side view of the package of FIG. 5.

DETAILED DESCRIPTION OF THE INVENTION

Figure 1:
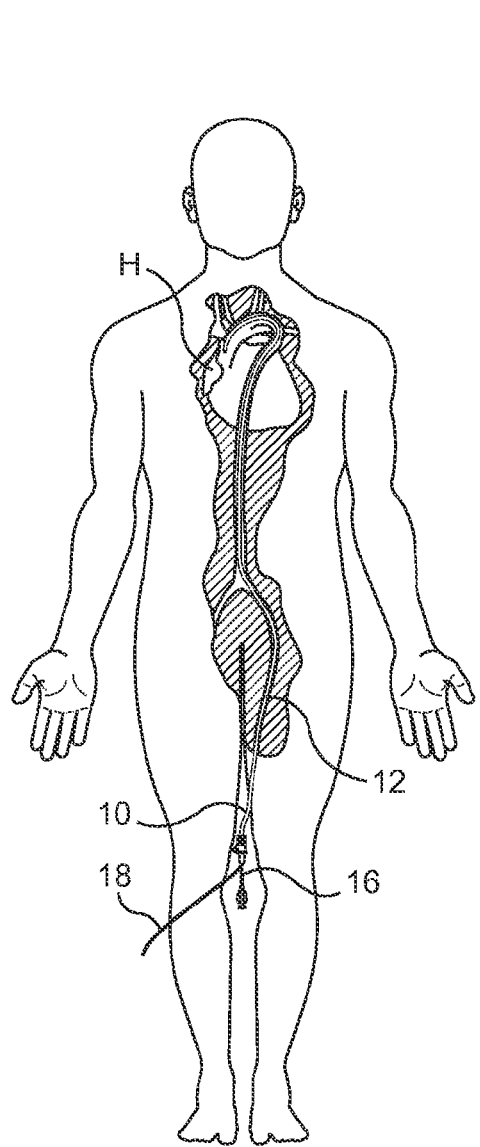
FIG. 1 is a diagrammatic illustration of the deployment of a treatment catheter within a patient's vasculature.
Figure 2:
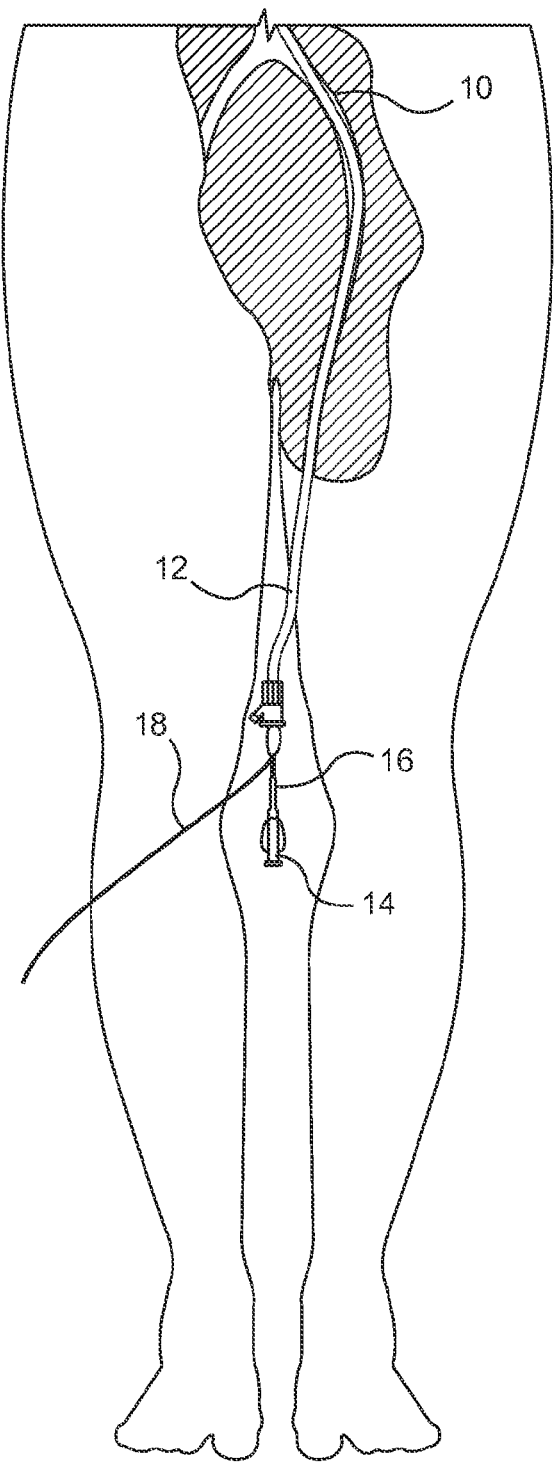
FIG. 2 is an enlarged view of a lower portion of FIG. 1.

Specific embodiments of the present invention are now described with reference to the figures, wherein like reference numbers indicate identical or functionally similar elements. While the disclosure refers to illustrative embodiments for particular applications, it should be understood that the disclosure is not limited thereto. Modifications can be made to the embodiments described herein without departing from the spirit and scope of the present disclosure. Those skilled in the art with access to this disclosure will recognize additional modifications, applications, and embodiments within the scope of this disclosure and additional fields in which the disclosed examples could be applied. Therefore, the following detailed description is not meant to be limiting. Further, it is understood that the systems and methods described below can be implemented in many different embodiments of hardware. Any actual hardware described is not meant to be limiting. The operation and behavior of the systems and methods presented are described with the understanding that modifications and variations of the embodiments are possible given the level of detail presented.

References to "one embodiment," "an embodiment," "in certain embodiments," etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

Embodiments hereof relate to a package for a catheter, or more generally, a package for a medical device having an elongated shaft. The package includes a one-piece or single body that eliminates the need to separately produce and subsequently assemble multiple components thereof. More particularly, prior art catheter packaging included various components or pieces, such as a coiled tube, retaining clips, a cannula holder, a loading tube, a finishing tube, and a looper, that were separately produced and subsequently assembled together. Embodiments hereof relate to a package that has a one-piece or unitary body, preferably formed by blow-molding to eliminate the need for one or more of these components, thereby reducing the number of separate components or pieces used for packaging a catheter. Although embodiments herein are primarily described for receiving a catheter that has an elongated tubular shaft and a proximal luer fitting, such packages may be used or modified to receive any type of medical device having an elongated shaft, such as but not limited to a guidewire, a sheath, an endoscope, or a microcatheter. The elongated shaft of the target medical device may define a lumen there-through or may be solid, with various cross-sectional sizes or shapes, and the target medical device may or may not include a proximal luer fitting. Further, when embodiments herein are utilized for receiving a catheter, the catheter may be any type of catheter and may or may not include a treatment element, e.g., a deflated balloon or compressed stent, at a distal end portion thereof. For example, embodiments hereof may be utilized to receive a diagnostic catheter or a guiding catheter, in addition to an interventional catheter having a treatment element at distal end portion thereof.

More particularly, with reference to FIGS. 5-12, a package or dispenser 30 includes a one-piece body 32 that is a single or unitary component, preferably formed by blow-molding. One-piece body 32 of package 30 may be fabricated from any suitable material that can be blow-molded, for example polypropylene, polyethylene, a nylon/polyethylene blend, polytetrafluoroethylene (PTFE), or any combination thereof. Blow molding is a manufacturing process by which hollow thermoplastic parts are formed. In advance of being introduced into a blow molding process, a parison or preform (not shown) is formed from a polymeric moldable material. The preform may have a tube-like shape with a hole or throat in one end through which compressed air can pass. A split mold having an internal cavity of a desired configuration or shape is closed around the parison. Pressurized air is then supplied to the parison, thereby inflating or pushing the polymeric material outward to conform to or match the shape of the internal cavity of the mold. The pressurized air may have a pressure in the range of 100 psi and 250 psi, and in one embodiment, is approximately 125 psi. The blow-molded component is then allowed to cool and shape set and thereafter the mold is opened and the blow-molded component is removed therefrom.

One or more secondary die cutting steps transform blow-molded article into one-piece body 32 of package 30. The die cutting steps described herein may be simultaneously performed in a single die cutting step, or may be sequentially performed in a die cutting operation having more than one step. In addition, as would be understood by one of ordinary skill in the art, alternative methods to die cutting may be used to remove material of blow-molded article including but not limited to punching, pinching off, trimming, water jetting, laser cutting, and other methods known in the art for removing or shaping a molded article.

Figure 5:
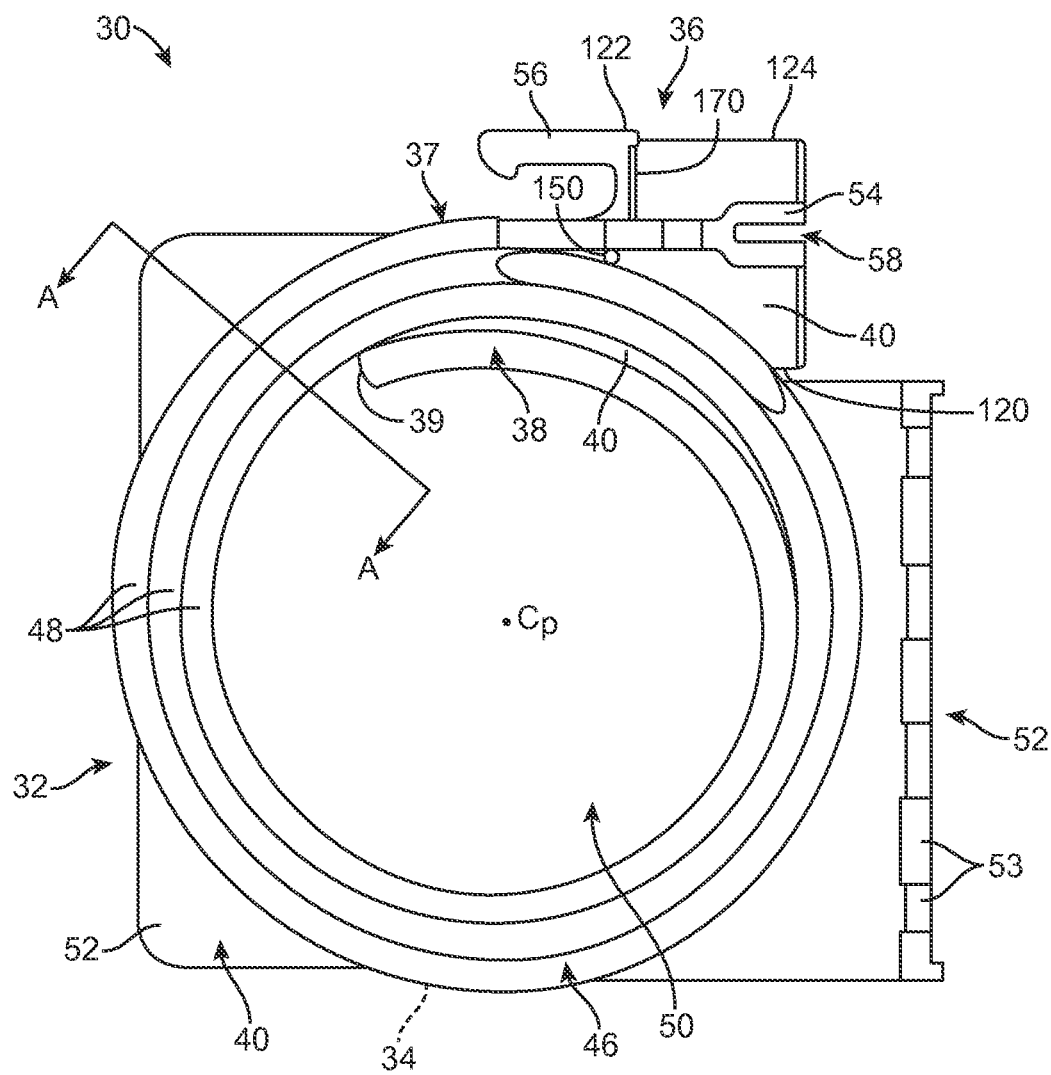
FIG. 5 is a top view of a package according to an embodiment of the present invention.
Figure 5A:
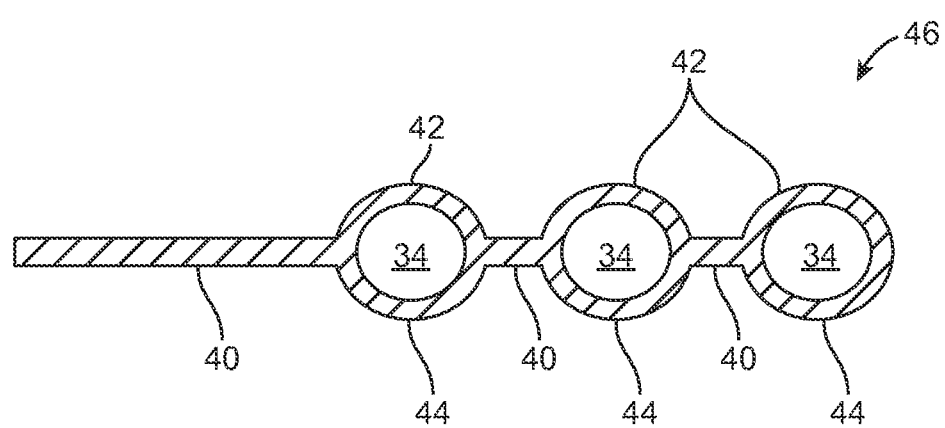
FIG. 5A is a cross-sectional view taken along line A-A of FIG. 5.

Blow-molded one-piece body 32 defines a spiral passageway or lumen 34 configured to receive an elongated shaft of a medical device or catheter to protect the medical device from undesired movement and potential damage during transport and storage. As shown in FIG. 5, body 32 has a luer retaining portion 36 at a first end 37 of lumen 34, and lumen 34 has a second end 38 with a closed end 39, such that second end is sealed off from the environment. More particularly, and as best shown in the cross-sectional view of FIG. 5A, one-piece body 32 includes webbing 40 disposed between a first or upper spiral rib or sidewall 42 and a second or lower spiral rib or sidewall 44. Upper and lower spiral ribs 42, 44 are raised or extend in opposing directions with respect to webbing 40 to collectively form a spiral casing 46 within which spiral lumen 34 is defined.

In the embodiment shown in FIG. 5, upper and lower spiral ribs 42, 44 each have a semi-circular cross-section such that spiral lumen 34 has a circular cross-section. However, the opposing upper and lower spiral ribs 42, 44 may have other configurations so that the spiral lumen 34 may be configured to have non-circular cross-sectional shapes, such as semi-circular or having a substantially flat or planar surface. In addition, it is not required that upper and lower spiral ribs 42, 44 have the same configuration. Although spiral casing 46 is shown with symmetric upper and lower spiral ribs 42, 44, the spiral casing 46 formed via blow-molding as described herein may have asymmetric upper and lower spiral ribs 42, 44.

As best shown in FIG. 5, radially adjacent curved portions 48, formed by upper and lower spiral ribs 42, 44 of spiral casing 46, are formed slightly spaced apart with webbing 40 extending therebetween. Stated another way, webbing 40 forms a bridging structure between adjacent curved portions 48. In this embodiment, webbing 40 is substantially flat or planar and the plurality of curved portions 48 of spiral casing 46 extend on a single or common plane, as best shown in the side views of FIGS. 6 and 6A. However, the webbing 40 may alternatively be curved or non-planar, in which webbing 40 extends between radially adjacent curved portions 48 of spiral casing 46 and is curved or non-planar. In addition, different lengths of elongate medical devices to be housed within package 30 may be accommodated by varying the overall diameter and/or turns of spiral casing 46 to adjust the length of lumen 34.

Spiral casing 46 includes a plurality of turns or curved portions 48 that are formed to spiral around a virtual center point $C_p$ of package 30. Although spiral casing 46 has an overall annular or ring-shaped molded form or profile, with curved portions 48 forming spiral curves or circles around center point $C_p$ of package 30, packages formed via blow-molding as described herein may have different forms or profiles. For example, as shown in FIG. 5, a distal region of second end 38 is formed to be substantially straight with an increased amount of webbing 40 disposed between adjacent curved portions 48. The advantage of this configuration is that selected, e.g. distal or proximal, portions of the medical device can be stored in a region of casing 46 that is completely straight, avoiding the potential for those portions of the device to take a curved set. In another embodiment, distal region of second end 38 is formed into a narrower profile to closely restrict movement of the distal end of a catheter during transportation.

In an embodiment, webbing 40 extends outwardly beyond spiral casing 46 to form a substantially square shaped one-piece body 32. In one embodiment, spiral casing 46 defines a circular void 50 with no webbing 40 formed therein. In another embodiment, webbing 40 has a thickened portion 52 on one side of body 32. As shown in FIGS. 5, 6 and 6A, thickened portion 52 is defined by a series of undulations 53 which help increase the thickness of webbing 40 on one side of body 32, thereby increasing the rigidity of webbing 40 and spiral casing 46. Webbing 40 provides rigidity to one-piece body 32 as well as providing structure for grasping or attaching a jacket sleeve or labeling jacket (not shown) to body 32.

Luer retaining portion 36 includes a luer retainer 54, described below, with webbing 40 surrounding luer retainer 54 and bridging the luer retainer 54 to spiral casing 46. Luer retaining portion 36 also includes a webbing extension which forms a hook portion 56 to allow an operator to hang package 30 for easy storage. In an embodiment, hook portion 56 and luer retaining portion 36 are not covered by a jacket sleeve or labeling cover.

Luer retainer 54 is disposed or positioned on package 30 to be at first end 37 of spiral casing 46. Luer retainer 54 defines an opening 58 that is in fluid communication with spiral lumen 34. Luer retainer 54 is configured to receive a proximal luer fitting of a medical device or catheter. When luer fitting 14 of catheter 16 is secured within luer retainer 54 of package 30, catheter 16 is protected from undesired movement and potential damage during transport and storage. Although catheter 16 includes luer fitting 14, it will be understood by those of ordinary skill in the art that package 30 may be modified to receive a catheter or other medical device having an elongated shaft that does not include a proximal luer fitting.

Figures 3, 4:
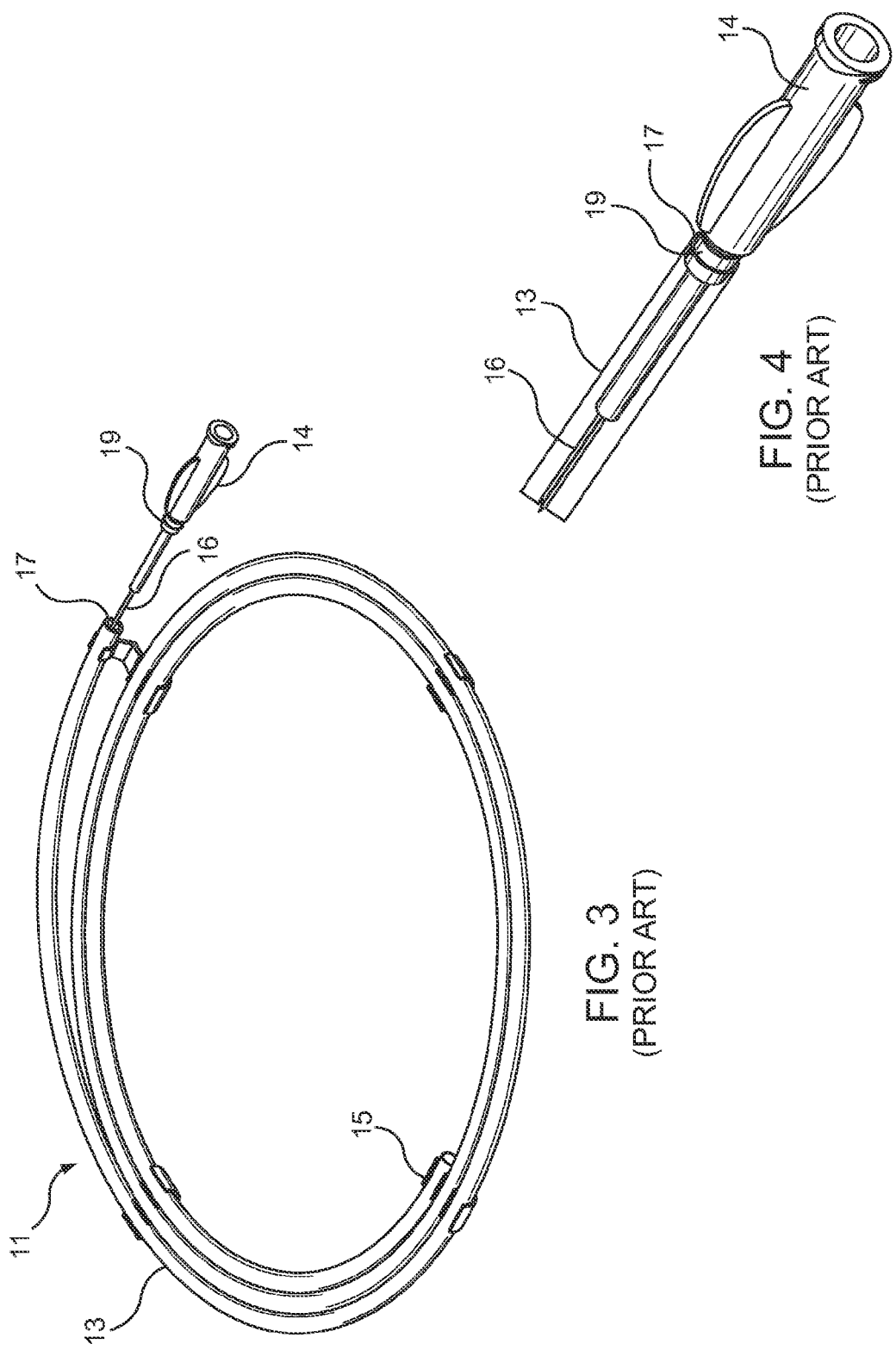
FIG. 3 is a perspective view of a conventional catheter packaging hoop with a catheter partially inserted into the hoop.
FIG. 4 is an enlarged view of a portion of the conventional catheter packaging hoop of FIG. 3 with the catheter fully inserted into the hoop.

By forming package 30 by blow-molding, one-piece body 32 thereof integrally includes spiral casing 46, webbing 40, luer retaining portion 36, and hook portion 56 to provide a reduction in part count and overall cost. Package 30 is also advantageously formed as a rigid one-piece component that lays flat for easy shipment and storage thereof, since adjacent curved portions 48 of spiral casing 46 extend on a common single plane and webbing 40 is integrally formed therebetween to interconnect the adjacent curved portions 48. Further, with adjacent curved portions 48 integrally formed as joined together via at least a portion of webbing 40, the need for retaining clips, such as those shown in FIG. 3, are not required to hold windings of coiled tubing together. Reducing the size and weight of the package further results in a shipping cost savings and thinner packages allows additional inventory to be stored within the same customer shelf space. In addition, package 30 having a one-piece body 32, is sterilized in a sterile environment using known methods without the need to further sterilize other components, thereby reducing the overall time of sterilization.

Figure 7:
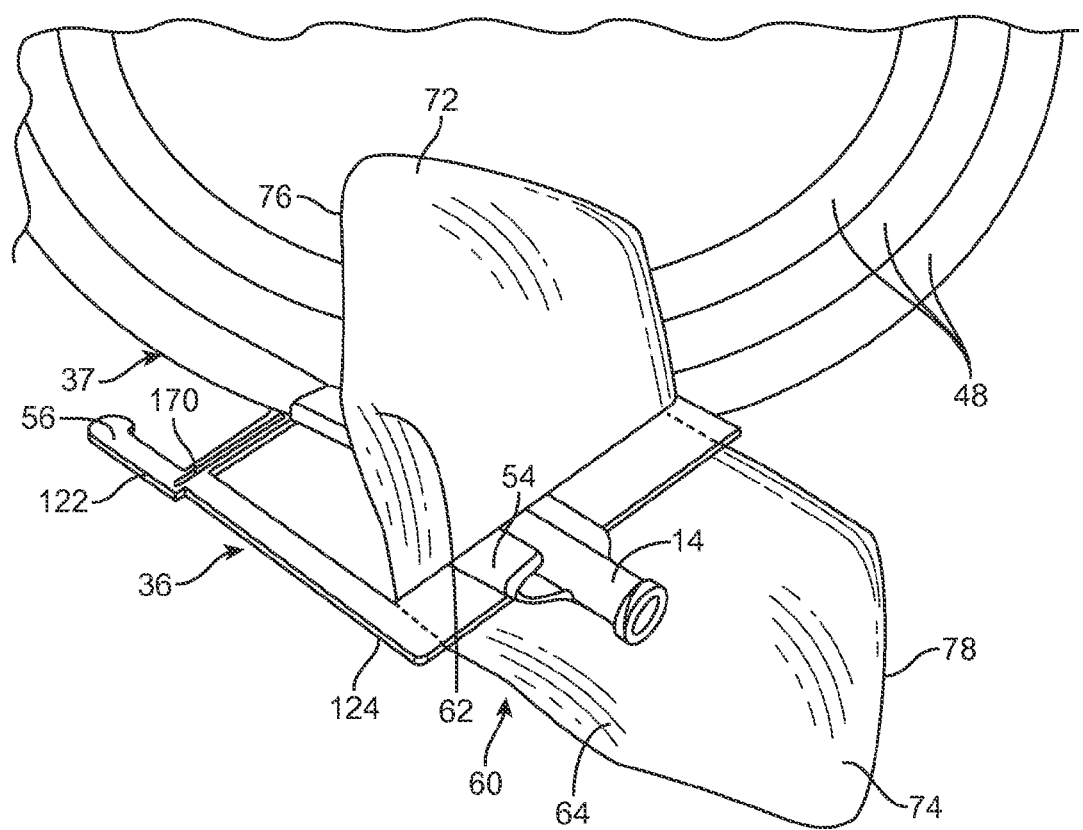
FIG. 7 is a perspective view of a portion of the package of FIG. 5, wherein two sheets of the barrier film are shown peeled apart.

FIG. 7 shows barrier film 60 which is sealed (in a sterile environment) directly to luer retaining portion 36 to maintain the sterility of the luer retaining portion 36, spiral casing 46, lumen 34 and the medical device disposed therein.

Figure 7A:
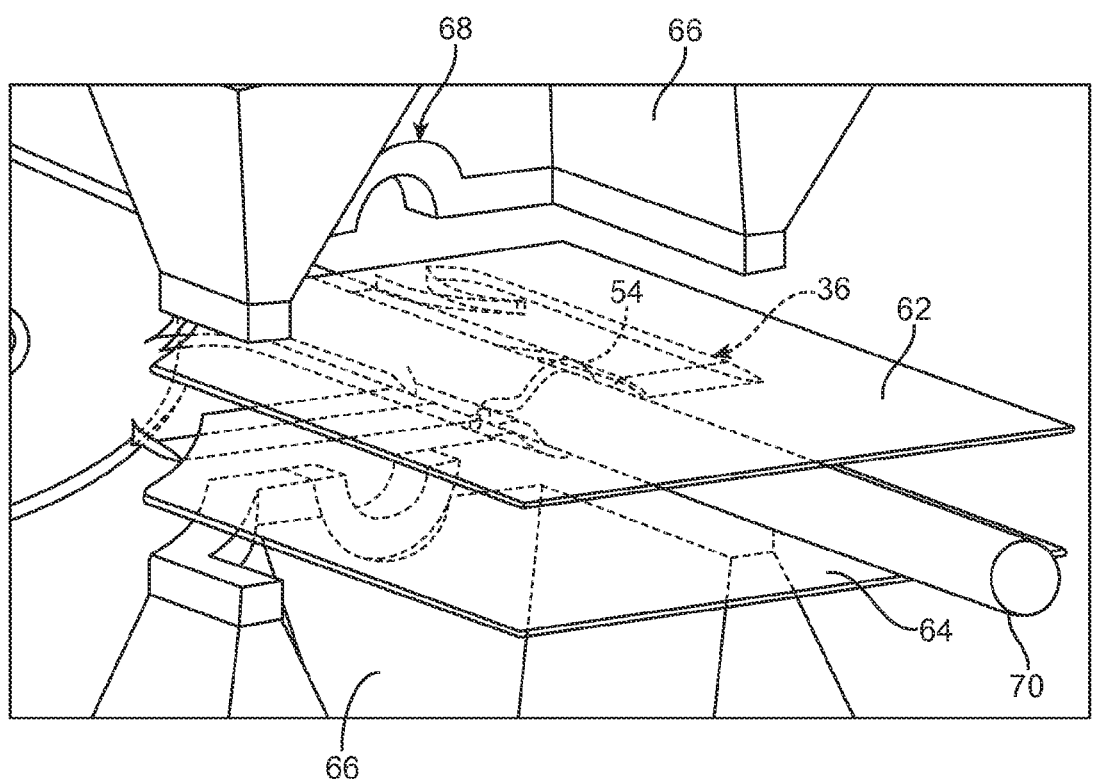
FIG. 7A illustrates a method of manufacturing of heat sealing the barrier film to the luer retaining portion of the package of FIG. 5.

Barrier film 60 can be either breathable or non-breathable depending on the sterilization process or product requirements. Barrier film 60 includes first and second sheets 62, 64 which are disposed on opposite sides of the luer retaining portion 36 and bonded together by adhesives, heat sealing or ultrasonic sealing. As shown in FIG. 7A, complimentary shaped sealing die 66 use heat and pressure to create a bond between sheets of barrier film 60. Die 66 each have a U-shaped portion 68 so that when die 66 are brought together, die 66 form a shape, in a complimentary manner, to accommodate the shape of luer retainer 54. A mandrel 70 is also used to provide structural support from within luer retainer lumen 34. A polypropylene layer is provided in between each sheet of barrier film 60 to bond the two sheets together during the sealing process.

Figure 8:
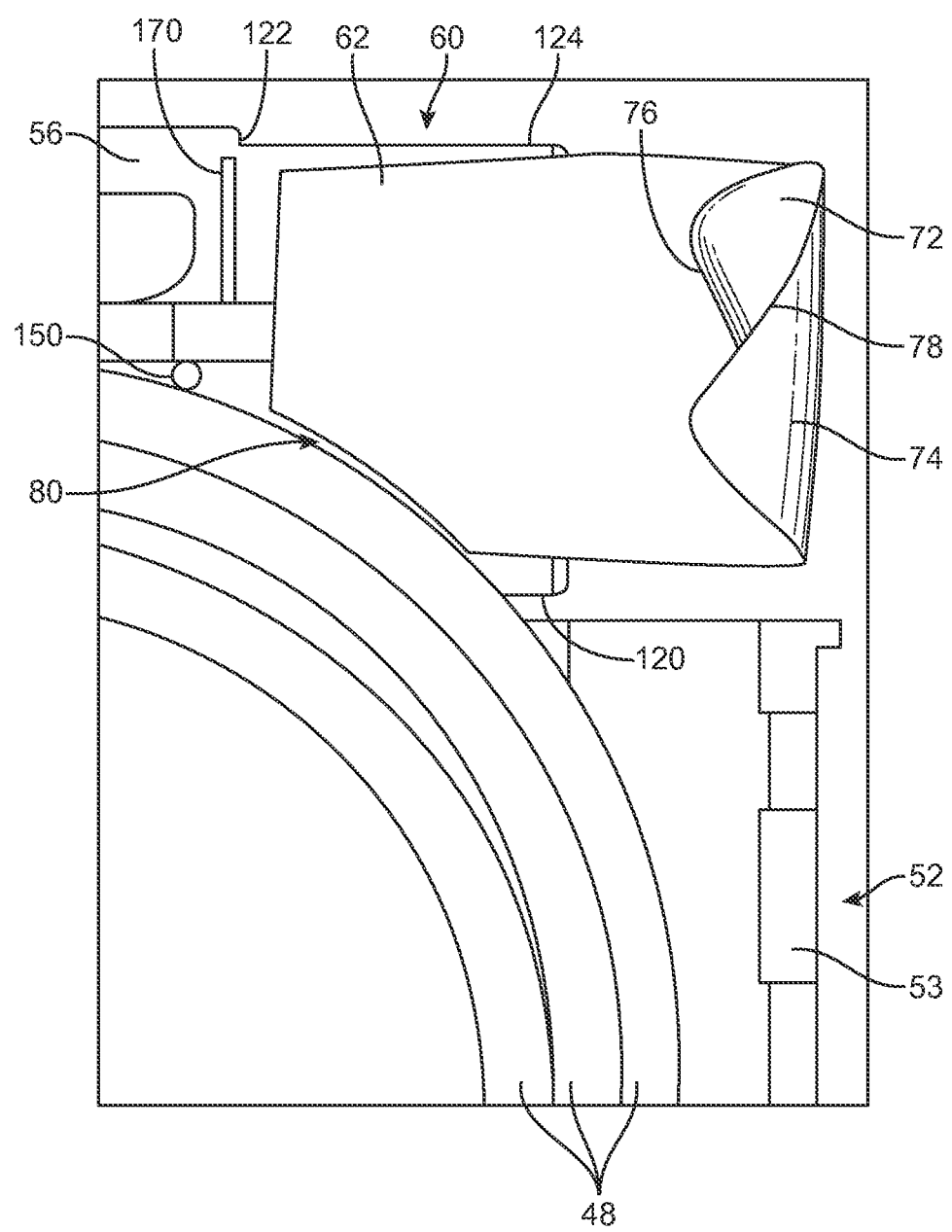
FIG. 8 is a top view of a portion of the package with the barrier film sealed onto the luer retaining portion of the package of FIG. 5.
Figure 13:
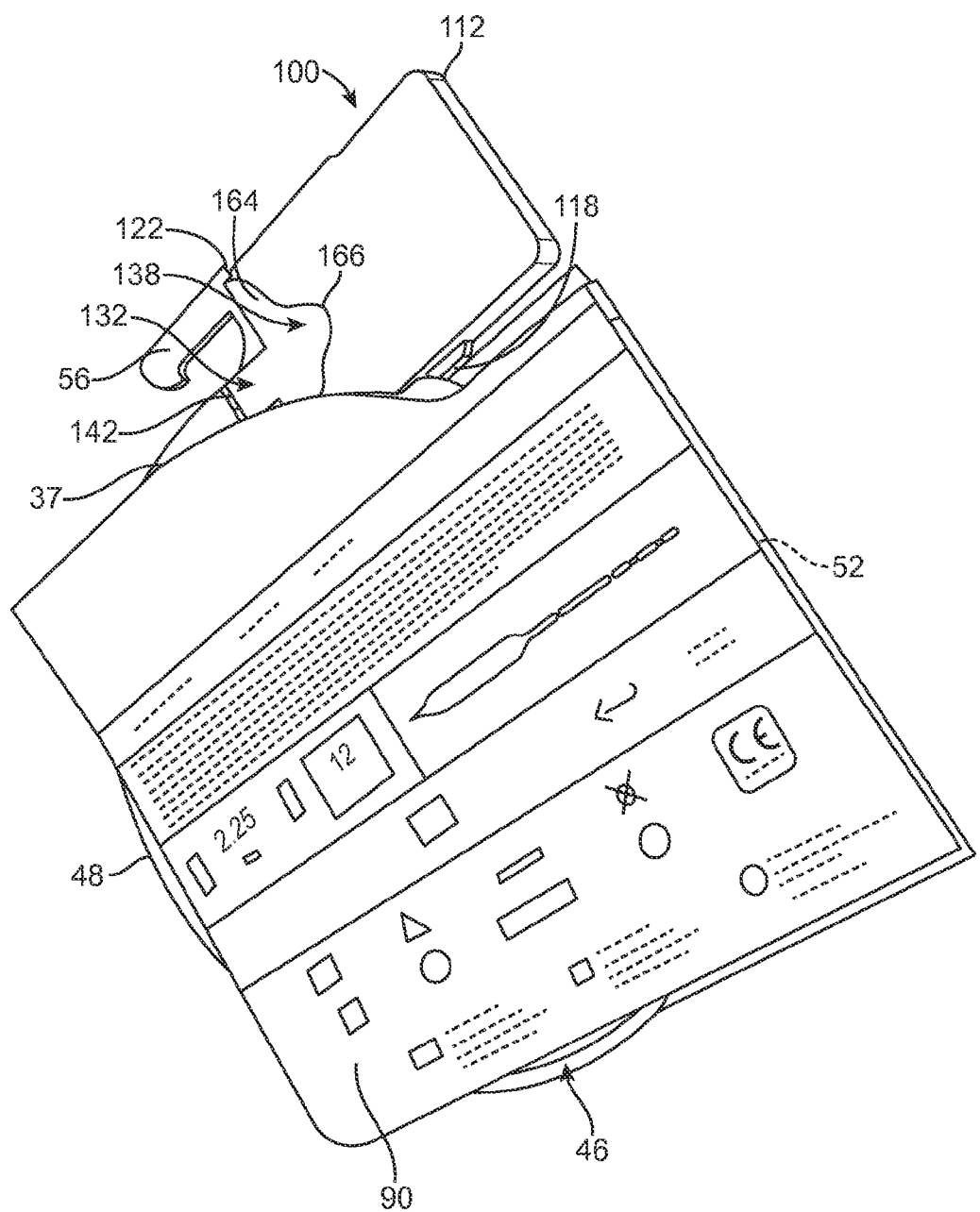
FIG. 13 is a perspective view of a flap partially covering the pouchless package.

Each sheet has tabs 72, 74, respectively, which are not sealed together. Tabs allow an operator to grasp each sheet 62, 64 of barrier film 60 and separate each sheet 62, 64 from each other to peel open the barrier film 60 to expose the luer retaining portion 36. In one embodiment, first sheet tab 72 has a substantially triangle shape with an edge 76 angled in a first direction. Second sheet tab 74 also has a substantially triangle shape but with an edge 78 angled in a second direction which is opposite to the first direction of the first sheet tab 72. As shown in FIG. 8, the mirrored shaped relationship of first and second sheet tabs 72, 74 allows tabs to fold over one side of barrier film 60 to better position tabs 72, 74 for easier grasping by the operator. In addition, folding tabs 72, 74 to one side prevents inadvertent separation of first and second sheets 62, 64 which may occur if both tabs 72, 74 are folded onto the exterior surfaces of first and second sheets 62, 64, respectively. In one embodiment, shown in FIG. 8, first and second surfaces of each sheet 62, 64 have different colors so that when tabs are folded over to one side of barrier film 60, tabs are differentiated from each other by contrasting color. As further shown in FIG. 8, barrier film 60 has an arcuate cutout 80 to conform with the curving spiral casing 46 once barrier film 60 is affixed to luer retaining portion 36. Thus, only barrier film 60 protects and maintains sterility of luer retaining portion 36, spiral casing 46, lumen 34 and the medical device disposed therein. As a result, barrier film 60 has eliminated the need for a pouch that would cover the entire package 30. In addition, the "pouchless" package 30 also removes the need for a box to completely encase a pouch, as is needed in the prior art. Instead, in an optional embodiment shown in FIG. 13, a flap 90 or other partial covering is coupled to package 30, for example to provide instructions, product identification of other indicia. Once the operator is ready to use the medical device, the operator grasps tabs 72, 74, peels open barrier film 60 by separating sheets 62, 64 and aseptically presents luer fitting 14 (or other proximal portion) into a sterile field for use of the medical device in a patient.

Figure 9:
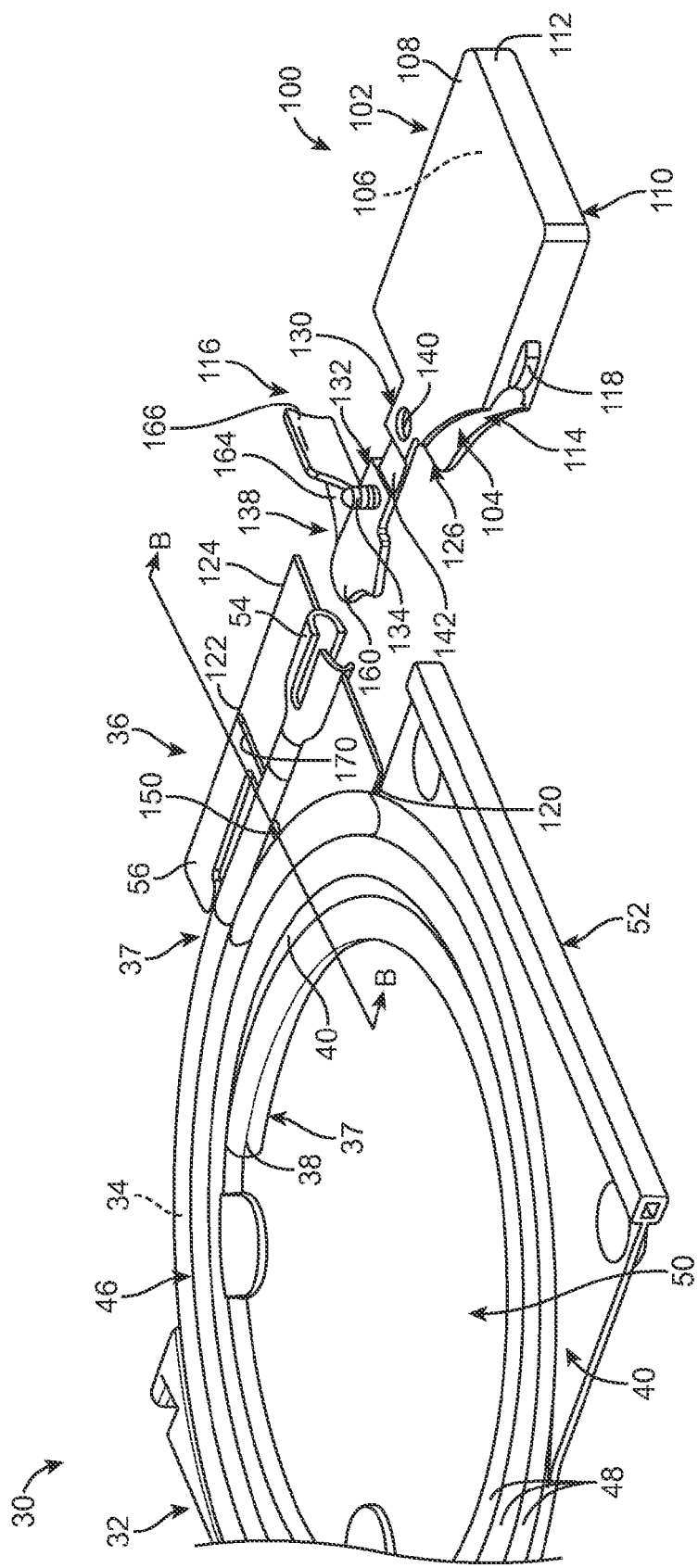
FIG. 9 is a perspective view of the package in relation to the cap before the cap covers the luer retaining portion.
Figure 10:
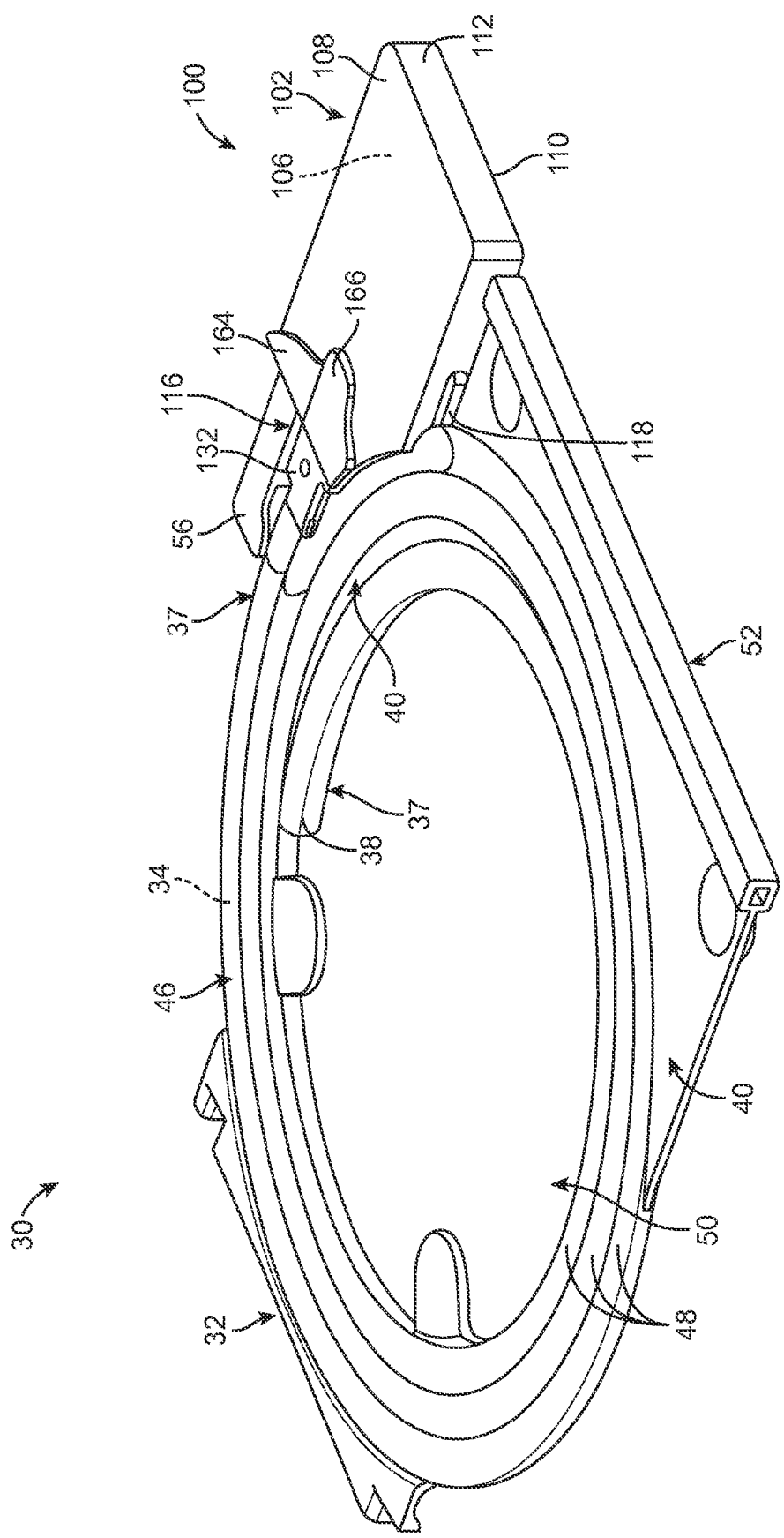
FIG. 10 is a perspective view of the package with the cap covering the luer retaining portion and the cap is locked onto the luer retaining portion.

FIG. 9 shows cap 100 configured to cover barrier film 60 and couple with one-piece body 32 to protect the integrity of the barrier film 60 from puncture or tearing during transport and storage. Cap 100 is sized and fitted to completely cover barrier film 60 and shielding film 60 at every angle from potentially harmful events, such as impacts and prevents objects from breaching barrier film 60. FIG. 10 shows cap 100 fully covering barrier film 60 and secured to luer retaining portion 36. Cap 100 includes a rigid housing 102 having an opening 104 and an interior surface which define a chamber 106 to receive luer retaining portion 36 with barrier film 60. Cap 100 is substantially rectangular shaped with first and second surfaces 108, 110 and a side surface 112 extending therebetween. In one embodiment, as shown in FIG. 9, opening 104 extends along one corner of cap 100 forming an arcuate cutout 114 in order to conform to the curving shape of spiral casing 46 when cap 100 is placed over luer retaining portion 36, as shown in FIG. 10. Cap 100 is designed to slide over luer retaining portion 36 with barrier film 60 and be releasable secured to luer retaining portion 36 by a lock member 116. Cap 100 housing has, on a side surface 112, at least a first guide portion 118 defining a groove (not shown) therein. The groove is in fluid communication with chamber 106. As cap 100 slides over luer retaining portion 36 and barrier film 60, an edge 120 of luer retaining portion 36 is received by groove and slides along the extent of groove until luer retaining portion 36 abuts guide portion 118 at the end of groove, thereby assisting the placement of cap 100 over luer retaining portion 36. Guide portion 118 also helps guide the operator to remove cap 100 from luer retaining portion 36 by sliding edge 120 of luer retaining portion 36 along the extent of groove until cap 100 is removed from luer retaining portion 36. In another embodiment, cap housing 102 has another guide portion 123 with a groove (not shown) on an opposite side surface 112 from guide portion 118. In this embodiment, an edge 124 of luer retaining portion 36 is received by groove and slides along the extent of groove until luer retaining portion 36 abuts guide portion 123 at the end of groove. In yet this same embodiment, hook portion 56 has a shoulder 122 for abutment with second guide portion to prevent cap 100 from sliding further over luer retaining portion 36. The interaction of guide portions 118, 123, edges 120, 124 and shoulder 122 helps to suspend film 60 within chamber 106 of cap 100 so as to reduce or eliminate contact between film 60 and interior surface of chamber 106.

Figure 9A:
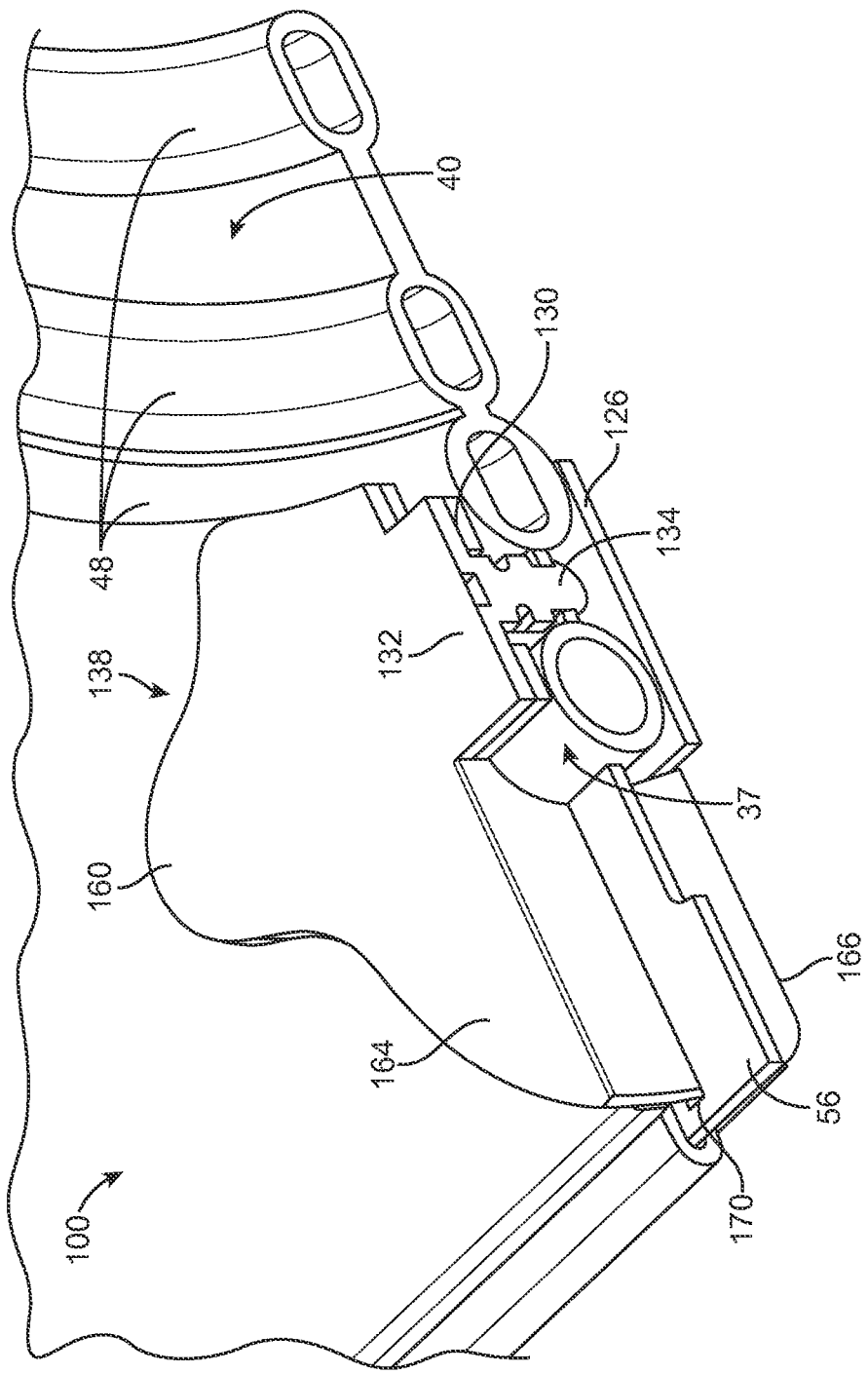
FIG. 9A is a cross-sectional view taken along line B-B of FIG. 9.

As shown in FIG. 9, lock member 116 extends from first surface 108 of cap 100 and second surface 110 has a rounded portion 126 extending therefrom. Lock member 116 has a living hinge portion 130, a pin portion 132 with a pin 134 extending therefrom and a clasp portion 138. Living hinge portion 130 has an opening 140 therethrough to receive pin 134 when pin portion 132 is rotated about a living hinge 142 until pin portion 132 contacts living hinge portion 130 with pin 134 extending through opening 140, as shown in FIG. 10. Since cap 100 completely covers barrier film 60, pin 134 extends through opening 140 in living hinge portion 130 and contacts webbing 40 of body 32. In one embodiment, webbing 40 of body 32 also has an opening 150 (shown in FIG. 9 and positioned, for example, between two adjacent curved portions 48) to receive pin 134 such that pin 134 extends through webbing 40 and further contacts rounded portion 126 of second surface 110. FIG. 9A is a cross-sectional view taken along line B-B in FIG. 9 and shows pin 134 disposed through living hinge portion 130 and through opening 150 in webbing 40 to contact rounded portion 126. In another embodiment, pin 134 is designed for only one time insertion into the openings 140, 150 of living hinge portion 130 or webbing 40, respectively. Thus, pin 134 would be scored or have a minimum diameter dimension 152 to induce fracture of pin 134 when clasp portions 132, 138 are rotated about living hinge 142 to extract or remove pin 134 from either openings 140, 150 of living hinge portion 130 or webbing 40. Thus, when the operator rotates clasp portion 132, 138 about living hinge in order to remove cap 100, an audible sound or click is heard by the operator indicating that pin 134 has fractured. The operator will also feel increased resistance until the pin snaps. The audible sound and increase resistance provide notice to the operator that this is the first time cap 100 has been removed from body 32 since cap 100 was secured to body 32 prior to sterilization, thereby providing assurances to the operator that the contents sealed by film 60 are still sterile. If the operator is unable to hear the audible sound, but nonetheless realizes that pin 134 is broken or fractured, the operator will know that pin or clasp portions 132, 138 have been rotated or damaged which would thereby provide notice to the operator that the cap 100 may have been removed and the sterility of barrier film 60 has been compromised.

Figure 11:
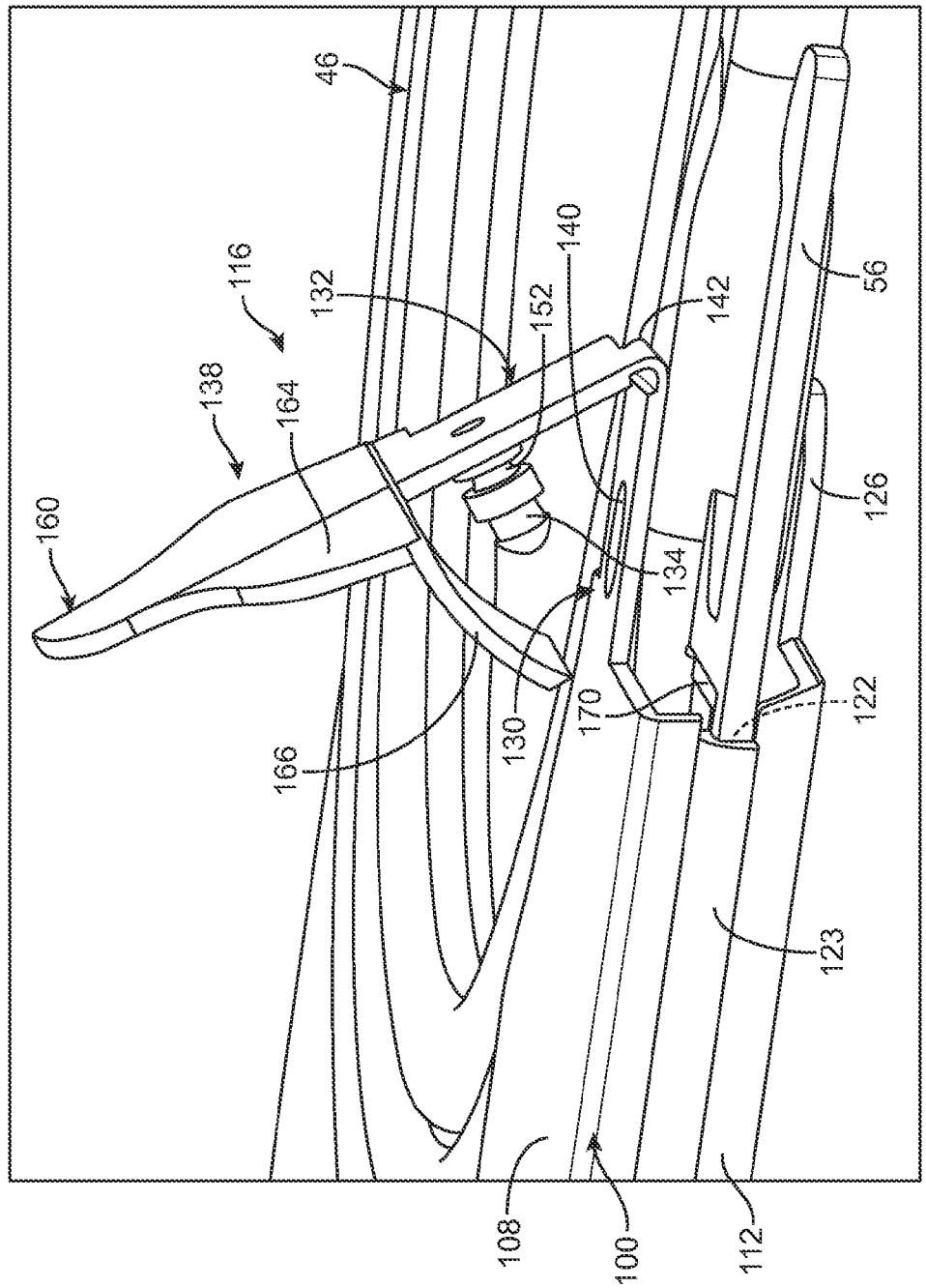
FIG. 11 is a perspective view of the locking member of the cap before the locking member is secured to the luer retaining portion.
Figure 12:
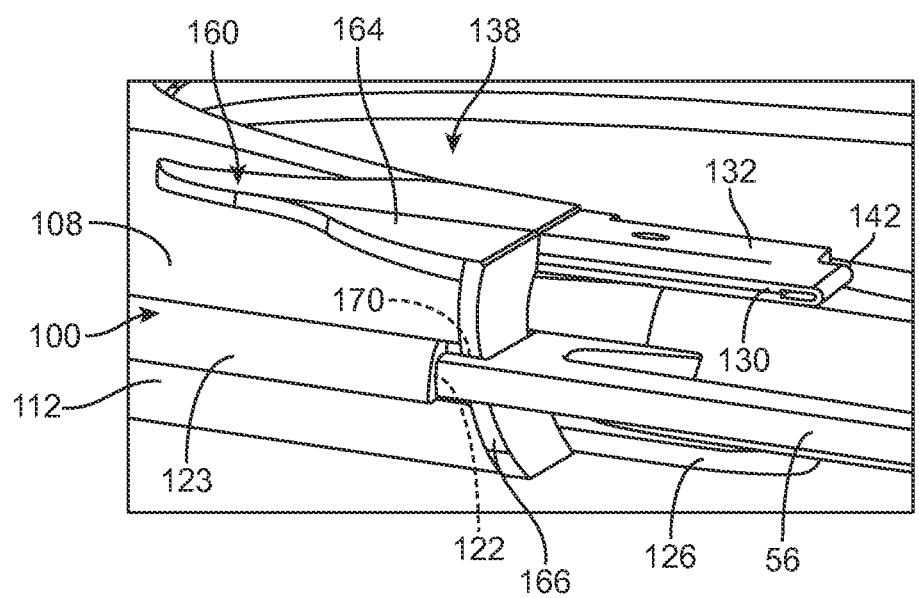
FIG. 12 is a perspective view of the locking member of the cap secured to the luer retaining portion.

As shown in FIGS. 9-12, clasp portion 138 has at least one rounded portion 160 for easy grasping by the operator to either insert into or extract pin 134 from the openings 140, 150 of living hinge portion 130 or webbing 40. Clasp portion 138 also has a clasp extension 164 with an arcuate tongue 166 extending substantially perpendicular from clasp extension 164. Tongue 166 extends from clasp extension 164 in substantially the same direction as pin 134. When clasp portion 138, along with pin portion 132 is rotated about living hinge 142, tongue 166 is received by a longitudinal opening 170 in webbing 40 of luer retaining portion 36. As shown in FIG. 9, longitudinal opening 170 is disposed adjacent hook portion 56 and opening 170 extends substantially perpendicular to edge 124 of luer retaining portion 36. As shown in FIG. 11, the arcuate shape of the tongue 166 allows tongue 166 to be fully received by longitudinal opening 170 at the same time as pin and clasp portions 132, 138 are being rotated about living hinge 142 toward first surface 108 of cap housing 102. As shown in FIG. 12, once pin and clasp portions 132, 138 have been folded over and in full contact with living hinge portion 132 and first surface 108 of cap housing 102, the arcuate shape of tongue 166 restricts the movement of pin and clasp portions 132, 138 to only rotational movement about living hinge 142. When tongue 166 is received within longitudinal opening, cap 100 is prevented from being removed from luer retaining portion 36 and barrier film 60, such as, for example, removing cap 100 by sliding guide portion 118 along edge 120 of luer retaining portion 36. In addition, as shown in FIGS. 9A and 12, tongue 166 closes opening 104 to chamber 106 of cap 100 effectively preventing foreign objects from entering chamber 106 of cap 100.

FURTHER EXAMPLES

The following examples are illustrative of several embodiments of the present technology:

1. A package for holding a medical device having an elongated shaft, the package comprising:
   a one-piece body that defines a spiral lumen configured to receive the elongated shaft of the medical device, the spiral lumen having a first end and a second sealed end, wherein the first end has a luer retaining portion;
   a barrier film sealed to the luer retaining portion to maintain sterility of the luer retaining portion; and
   a cap releasably secured to the luer retaining portion to cover and protect the barrier film.
2. The package of example 1, wherein the luer retainer portion defines an opening configured to receive a proximal luer fitting of the medical device.
3. The package of any of examples 1 and 2, wherein the luer retainer portion has a hook portion extending therefrom, the hook portion spaced apart from the spiral lumen.
4. The package of any of the preceding examples, wherein the barrier film includes two sheets sealed together on each side of the luer retainer portion.
5. The package of example 4, wherein the two sheets each have a tab portion, the tab portions are not sealed together and are configured to allow an operator to grasp the tab portions and peel apart the two sheets to aseptically present the luer retaining portion.
6. The package of any of the preceding examples, wherein the cap has a housing defining a chamber to receive the luer retaining portion with the barrier film sealed thereon.
7. The package of any of the preceding examples, wherein the cap has a locking member to releasably secure the cap to the luer retaining portion.
8. The package of example 7, wherein the locking member has a living hinge portion and a pin portion, the pin portion having a pin extending substantially perpendicular from a surface of the pin portion, the living hinge portion having an opening therethrough to receive the pin when pin portion is rotated about a living hinge such that the pin extends through the opening of the living hinge portion and contacts the luer retaining portion.
9. The package of example 8, wherein the locking member has a clasp portion extending from the pin portion, the clasp portion has an arcuate tongue extending substantially perpendicular from a surface of the clasp portion, such that as the pin and clasp portion are rotated about the living hinge, the tongue is received by an opening in the luer retaining portion and thereby secures the cap to the luer retaining portion by restricting the movement of the pin and clasp portions to only rotational movement about the living hinge.
10. The package of example 1 further comprising:
   a unitary body defining a spiral lumen configured to receive the elongated shaft of the medical device, the spiral lumen having a first end and a second sealed end, wherein the second end has a closed distal tip and the first end has a luer retaining portion, wherein the luer retainer portion defines an opening configured to receive a proximal luer fitting of the medical device;
   a barrier film including two sheets sealed together by heat sealing with the luer retaining portion disposed therebetween to maintain sterility of the proximal luer fitting; and
   a cap releasably secured to the luer retaining portion to cover and protect the barrier film,
   wherein the cap includes a housing defining a chamber, the cap configured to slidably receive the luer retaining portion with the barrier film within the chamber, the cap is secured to the luer retaining portion with a releasable locking member extending from the cap.
11. The package of example 10, wherein the wherein the package is configured such that the two sheets are sealed between sealing die, the sealing die each have U-shaped portions which are configured such that when the die come together, the die form a shape which accommodates the shape of a luer retainer of the luer retaining portion.
12. The package of example 11 or 12, wherein a mandrel is disposed within the luer retainer to provide structural support from within luer retainer.
13. The package of example 11, wherein a polypropylene layer is disposed between the two sheets to create a bond between the two sheets during the sealing process.
14. The package of any of examples 10 to 13, wherein the cap housing has at least one guide portion defining a groove in fluid communication with the chamber, and is configured such that as the cap is placed on the luer retaining portion, the groove receives an edge of the luer retaining portion, and the luer retaining portion slides along the extent of groove until the edge of the luer retaining portion abuts the guide portion at the end of the groove.
15. The package of example 14, wherein the at least one guide portion suspends barrier film within the chamber of the cap to minimize contact between the barrier film and an interior surface of the chamber.

16. The package of any of examples 10 to 15, wherein the locking member is configured such that it secures the cap to the luer retaining portion by rotating a clasp portion about a living hinge to connect the clasp portion to the locking member.

17. The package of example 16, wherein the locking member has an opening for releasably receiving a pin extending from the clasp portion.

18. The package of example 17, wherein it is configured such that if the clasp portion is rotated about the living hinge to remove the pin from the opening, the pin fractures and the clasp portion is no longer connected to the luer retaining portion.

19. The package of any of examples 16 to 18, wherein the clasp portion further includes an arcuate tongue receivable within an opening of the luer retaining portion to prevent removal of the cap from the luer retaining portion.

20. The package of example 10, further configured such that the locking member may be released to unsecure the cap from the luer retaining portion and the cap may be removed from the luer retaining portion.

21. The package of example 20, further configured such that the two sheets of the barrier film may be separated to aseptically present the proximal luer fitting.

While various embodiments according to the present invention have been described above, it should be understood that they have been presented by way of illustration and example only, and not limitation. It will be apparent to persons skilled in the relevant art that various changes in form and detail can be made therein without departing from the spirit and scope of the invention. Thus, the breadth and scope of the present invention should not be limited by any of the above-described exemplary embodiments. It will also be understood that each feature of each embodiment discussed herein, and of each reference cited herein, can be used in combination with the features of any other embodiment.

What is claimed is:

1. A package for holding a medical device having an elongated shaft, the package comprising:
   a one-piece body that defines a spiral lumen configured to receive the elongated shaft of the medical device, the spiral lumen having a first end and a second sealed end, wherein the first end has a luer retaining portion;
   a barrier film sealed to the luer retaining portion to maintain sterility of the luer retaining portion; and
   a cap releasably secured to the luer retaining portion to cover and protect the barrier film.

2. The package of claim 1, wherein the luer retainer portion defines an opening configured to receive a proximal luer fitting of the medical device.

3. The package of claim 1, wherein the luer retainer portion has a hook portion extending therefrom, the hook portion spaced apart from the spiral lumen.

4. The package of claim 1, wherein the barrier film includes two sheets sealed together on each side of the luer retainer portion.

5. The package of claim 4, wherein the two sheets each have a tab portion, the tab portions are not sealed together and are configured to allow an operator to grasp the tab portions and peel apart the two sheets to aseptically present the luer retaining portion.

6. The package of claim 1, wherein the cap has a housing defining a chamber to receive the luer retaining portion with the barrier film sealed thereon.

7. The package of claim 1, wherein the cap has a locking member to releasably secure the cap to the luer retaining portion.

8. The package of claim 7, wherein the locking member has a living hinge portion and a pin portion, the pin portion having a pin extending substantially perpendicular from a surface of the pin portion, the living hinge portion having an opening therethrough to receive the pin when pin portion is rotated about a living hinge such that the pin extends through the opening of the living hinge portion and contacts the luer retaining portion.

9. The package of claim 8, wherein the locking member has a clasp portion extending from the pin portion, the clasp portion has an arcuate tongue extending substantially perpendicular from a surface of the clasp portion, such that as the pin and clasp portion are rotated about the living hinge, the tongue is received by an opening in the luer retaining portion and thereby secures the cap to the luer retaining portion by restricting the movement of the pin and clasp portions to only rotational movement about the living hinge.

10. A package for holding a medical device having an elongated shaft, the package comprising:
    a unitary body defining a spiral lumen configured to receive the elongated shaft of the medical device, the spiral lumen having a first end and a second sealed end, wherein the second end has a closed distal tip and the first end has a luer retaining portion, wherein the luer retainer portion defines an opening configured to receive a proximal luer fitting of the medical device;
    a barrier film including two sheets sealed together by heat sealing with the luer retaining portion disposed therebetween to maintain sterility of the proximal luer fitting; and
    a cap releasably secured to the luer retaining portion to cover and protect the barrier film,
    wherein the cap includes a housing defining a chamber, the cap configured to slidably receive the luer retaining portion with the barrier film within the chamber, the cap is secured to the luer retaining portion with a releasable locking member extending from the cap.

11. The package of claim 10, wherein the wherein the package is configured such that the two sheets are sealed between sealing die, the sealing die each have U-shaped portions which are configured such that when the die come together, the die form a shape which accommodates the shape of a luer retainer of the luer retaining portion.

12. The package of claim 11, wherein a mandrel is disposed within the luer retainer to provide structural support from within luer retainer.

13. The package of claim 11, wherein a polypropylene layer is disposed between the two sheets to create a bond between the two sheets during the sealing process.

14. The package of claim 10, wherein the cap housing has at least one guide portion defining a groove in fluid communication with the chamber, and is configured such that as the cap is placed on the luer retaining portion, the groove receives an edge of the luer retaining portion, and the luer retaining portion slides along the extent of groove until the edge of the luer retaining portion abuts the guide portion at the end of the groove.

15. The package of claim 14, wherein the at least one guide portion suspends barrier film within the chamber of the cap to minimize contact between the barrier film and an interior surface of the chamber.

16. The package of claim 10, wherein the locking member is configured such that it secures the cap to the luer retaining portion by rotating a clasp portion about a living hinge to connect the clasp portion to the locking member.

17. The package of claim 16, wherein the locking member has an opening for releasably receiving a pin extending from the clasp portion.

18. The package of claim 17, wherein it is configured such that if the clasp portion is rotated about the living hinge to remove the pin from the opening, the pin fractures and the clasp portion is no longer connected to the luer retaining portion.

19. The package of claim 16, wherein the clasp portion further includes an arcuate tongue receivable within an opening of the luer retaining portion to prevent removal of the cap from the luer retaining portion.

20. The package of claim 10, further configured such that the locking member may be released to unsecure the cap from the luer retaining portion and the cap may be removed from the luer retaining portion.

21. The package of claim 20, further configured such that the two sheets of the barrier film may be separated to aseptically present the proximal luer fitting.

\* \* \* \* \*